United States Patent
Koseoglu et al.

(10) Patent No.: US 11,473,022 B2
(45) Date of Patent: Oct. 18, 2022

(54) DISTILLATE HYDROCRACKING PROCESS WITH AN N-PARAFFINS SEPARATION STEP TO PRODUCE A HIGH OCTANE NUMBER ISOMERATE STREAM AND A STEAM PYROLYSIS FEEDSTOCK

(71) Applicant: Saudi Arabian Oil Company, Dhahran (SA)

(72) Inventors: Omer Refa Koseoglu, Dhahran (SA); Ashok Kumar Punetha, Dhahran (SA)

(73) Assignee: Saudi Arabian Oil Company, Dhahran (SA)

( * ) Notice: Subject to any disclaimer, the term of this patent is extended or adjusted under 35 U.S.C. 154(b) by 0 days.

(21) Appl. No.: 17/143,286

(22) Filed: Jan. 7, 2021

(65) Prior Publication Data
US 2022/0213396 A1   Jul. 7, 2022

(51) Int. Cl.
*C10G 65/12*   (2006.01)
*C10G 69/06*   (2006.01)
*C07C 4/06*    (2006.01)

(52) U.S. Cl.
CPC ............... *C10G 65/12* (2013.01); *C07C 4/06* (2013.01); *C10G 69/06* (2013.01); *C10G 2300/1055* (2013.01); *C10G 2300/202* (2013.01); *C10G 2300/301* (2013.01); *C10G 2300/308* (2013.01); *C10G 2300/4006* (2013.01);
(Continued)

(58) Field of Classification Search
CPC .. C10G 65/12; C10G 69/06; C10G 2300/301; C10G 2400/02; C10G 2400/20; C10G 2300/4012; C10G 2300/1055; C10G 2300/4006; C10G 2300/308; C10G 2300/4018; C10G 2300/202; C07C 4/06
See application file for complete search history.

(56) References Cited

U.S. PATENT DOCUMENTS 3,074,878 A   1/1963   Pappas
3,132,087 A   5/1964   Kelley et al.
(Continued)

FOREIGN PATENT DOCUMENTS

CN   107177374 B   1/2019
CN   109718760 A   5/2019
(Continued)

OTHER PUBLICATIONS

Office Action dated Jun. 18, 2021 pertaining to U.S. Appl. No. 17/143,296, filed Jan. 7, 2021, 17 pages.
(Continued)

*Primary Examiner* — Thuan D Dang
(74) *Attorney, Agent, or Firm* — Dinsmore & Shohl LLP

(57) ABSTRACT

In accordance with one or more embodiments of the present disclosure, process for reforming a diesel feedstock to convert diesel to a gasoline blending component includes hydrodesulfurizing and hydrodenitrogenizing the diesel feedstock to reduce a sulfur content of the diesel feedstock and a nitrogen content of the diesel feedstock; hydrocracking the hydrodesulfurized and hydrodenitrogenized diesel feedstock over a metal-containing diesel hydrocracking catalyst comprising at least one zeolite to produce an isomerate fraction; and separating the isomerate fraction into a first stream enriched in n-paraffins and a second stream enriched in iso-paraffins and naphthenes.

18 Claims, 1 Drawing Sheet

(52) U.S. Cl.
CPC ............... *C10G 2300/4012* (2013.01); *C10G 2300/4018* (2013.01); *C10G 2400/02* (2013.01); *C10G 2400/20* (2013.01)

(56) References Cited

U.S. PATENT DOCUMENTS

| | | | |
|---|---|---|---|
| 3,159,568 | A | 12/1964 | Price et al. |
| 3,210,264 | A | 10/1965 | Haney |
| 3,240,694 | A | 3/1966 | Mason et al. |
| 3,305,476 | A | 2/1967 | York et al. |
| 3,420,768 | A | 1/1969 | Bray et al. |
| 3,702,292 | A | 11/1972 | Bunch |
| 3,758,403 | A | 9/1973 | Rosinski et al. |
| 3,758,628 | A | 9/1973 | Strickland et al. |
| 3,894,931 | A | 7/1975 | Nace et al. |
| 3,894,933 | A | 7/1975 | Owen et al. |
| 3,894,934 | A | 7/1975 | Owen et al. |
| 4,176,053 | A | 11/1979 | Holcombe |
| 4,394,301 | A | 7/1983 | Gardner |
| 4,419,221 | A | 12/1983 | Castagnos, Jr. et al. |
| 4,476,345 | A | 10/1984 | Gray, Jr. et al. |
| 4,695,368 | A | 9/1987 | Ward |
| 4,713,167 | A | 12/1987 | Reno et al. |
| 4,789,457 | A | 12/1988 | Fischer et al. |
| 4,826,587 | A | 5/1989 | Ward et al. |
| 4,828,676 | A | 5/1989 | Sawyer et al. |
| 4,913,799 | A | 4/1990 | Gortsema et al. |
| 4,950,384 | A | 8/1990 | Groeneveld et al. |
| 4,980,053 | A | 12/1990 | Li et al. |
| 5,026,472 | A | 6/1991 | Hoehn et al. |
| 5,147,526 | A | 9/1992 | Kukes et al. |
| 5,326,465 | A | 7/1994 | Yongqing et al. |
| 5,364,514 | A | 11/1994 | Sanborn et al. |
| 5,462,652 | A | 10/1995 | Wegerer |
| 5,863,315 | A | 1/1999 | Jullian et al. |
| 5,885,440 | A | 3/1999 | Hoehn et al. |
| 5,904,835 | A | 5/1999 | Thakkar |
| 6,113,775 | A | 9/2000 | Christolini et al. |
| 6,217,746 | B1 | 4/2001 | Thakkar et al. |
| 6,312,586 | B1 | 11/2001 | Kalnes et al. |
| 6,478,952 | B1 | 11/2002 | Lin |
| 6,656,346 | B2 | 12/2003 | Ino et al. |
| 7,271,303 | B1 | 9/2007 | Sechrist et al. |
| 9,464,241 | B2 | 10/2016 | Koseoglu et al. |
| 10,053,401 | B1 | 8/2018 | Beadle et al. |
| 10,093,873 | B2 | 10/2018 | Koseoglu et al. |
| 2003/0006168 | A1 | 1/2003 | Ino et al. |
| 2006/0021912 | A1* | 2/2006 | Chen ..................... C10G 11/05 208/120.01 |
| 2007/0272593 | A1 | 11/2007 | Stockwell et al. |
| 2009/0159494 | A1 | 6/2009 | Gautam et al. |
| 2009/0283442 | A1 | 11/2009 | McCall et al. |
| 2009/0288985 | A1 | 11/2009 | Long et al. |
| 2012/0016167 | A1* | 1/2012 | Hanks ..................... C10G 3/50 585/14 |
| 2013/0259764 | A1* | 10/2013 | Zimmerman .......... C10G 65/12 422/187 |
| 2013/0291432 | A1 | 11/2013 | Al-Therwi et al. |
| 2014/0171704 | A1* | 6/2014 | Erisken ................. C10G 11/00 585/303 |
| 2014/0275673 | A1 | 9/2014 | Long et al. |
| 2014/0357913 | A1 | 12/2014 | Funk et al. |
| 2015/0045598 | A1 | 2/2015 | Funk et al. |
| 2015/0141725 | A1 | 5/2015 | Lippmann et al. |
| 2015/0284644 | A1 | 10/2015 | Fanget et al. |
| 2018/0223197 | A1 | 8/2018 | Al-Ghamdi et al. |
| 2019/0040328 | A1 | 2/2019 | Koseoglu |
| 2019/0203130 | A1 | 7/2019 | Mukherjee |
| 2020/0102509 | A1 | 4/2020 | Bhuwania et al. |

FOREIGN PATENT DOCUMENTS

| | | |
|---|---|---|
| CN | 110591759 A | 12/2019 |
| EP | 0512635 B2 | 11/1992 |
| EP | 3536765 A1 | 9/2019 |
| WO | 2020205210 A1 | 10/2020 |

OTHER PUBLICATIONS

U.S. Office Action dated Sep. 30, 2021 pertaining to U.S. Appl. No. 17/149,789, filed Jan. 15, 2021, 23 pages.

International Search Report and Written Opinion dated Sep. 28, 2021 pertaining to International application No. PCT/US2021/020784 filed Mar. 4, 2021, 12 pages.

International Search Report and Written Opinion dated Feb. 24, 2022 pertaining to International application No. PCT/US2021/058505 filed Nov. 9, 2021, 14 pages.

U.S. Office Action dated Apr. 22, 2022 pertaining to U.S. Appl. No. 17/149,789, filed Jan. 15, 2021, 23 pages.

U.S. Office Action dated Nov. 24, 2021 pertaining to U.S. Appl. No. 17/143,296, filed Jan. 7, 2021, 23 pages.

Notification of Transmittal of the International Search Report and the Written Opinion of the International Searching Authority, or the Declaration dated Apr. 5, 2022 pertaining to International application No. PCT/US2022/011025 filed Jan. 3, 2022, 12 pages.

* cited by examiner

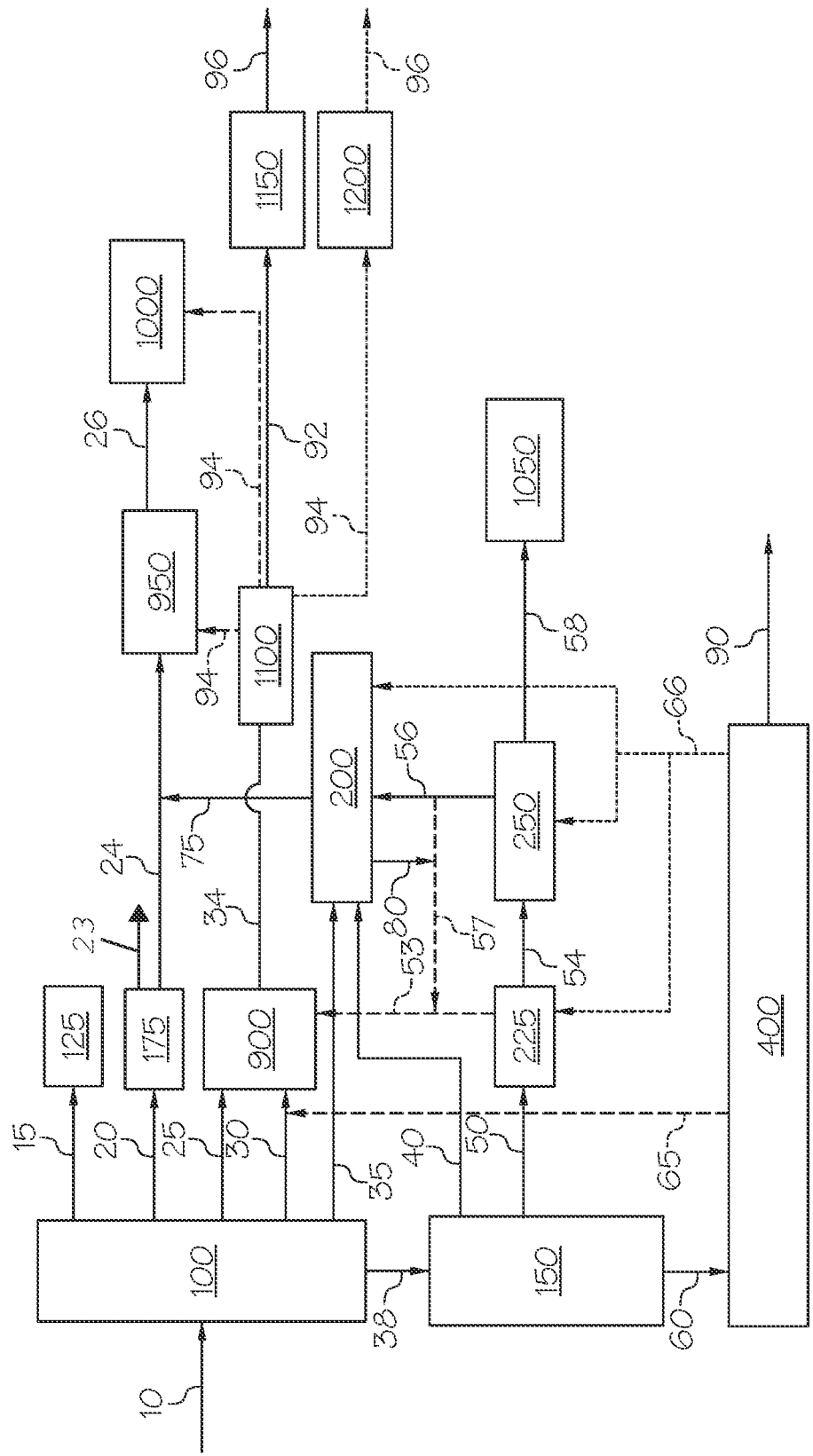

DISTILLATE HYDROCRACKING PROCESS WITH AN N-PARAFFINS SEPARATION STEP TO PRODUCE A HIGH OCTANE NUMBER ISOMERATE STREAM AND A STEAM PYROLYSIS FEEDSTOCK

FIELD

Embodiments of the present disclosure generally relate to hydrocracking of hydrocarbon oil, and pertain particularly to a process for reforming a diesel feedstock to convert diesel to a gasoline blending component.

TECHNICAL BACKGROUND

Hydrocracking processes are used commercially in a large number of petroleum refineries to process a variety of hydrocarbon feeds boiling in the range of 370° C. to 520° C. in conventional hydrocracking units and boiling at 520° C. and above in residue hydrocracking units. In general, hydrocracking processes split the molecules of the hydrocarbon feed into smaller, i.e., lighter, molecules having higher average volatility and economic value. Additionally, hydrocracking processes typically improve the quality of the hydrocarbon feedstock by increasing the hydrogen-to-carbon ratio and by removing organosulfur and organonitrogen compounds. Current hydrocracking processes lead to a surplus of diesel, and market conditions drive research efforts to convert diesel into value added products, such as ethylene, propylene, butylenes, and aromatics (benzene, toluene, and xylenes).

SUMMARY

There is a continual need for more effective processes for converting diesel into value added products. It has been discovered that a process that includes a step of separating a hydrocracked diesel isomerate fraction into an n-paraffins-rich stream and an iso-paraffins-rich stream, may greatly enhance the effectiveness of reforming the diesel into value added products.

According to one embodiment, a process for reforming a diesel feedstock to convert diesel to a gasoline blending component includes hydrodesulfurizing and hydrodenitrogenizing the diesel feedstock to reduce a sulfur content of the diesel feedstock and a nitrogen content of the diesel feedstock; hydrocracking the hydrodesulfurized and hydrodenitrogenized diesel feedstock over a metal-containing diesel hydrocracking catalyst comprising at least one zeolite to produce an isomerate fraction; and separating the isomerate fraction into a first stream enriched in n-paraffins and a second stream enriched in iso-paraffins and naphthenes.

According to one embodiment, a process for reforming a diesel feedstock to convert diesel to a gasoline blending component includes introducing the diesel feedstock to a treater for hydrodesulfurizing and hydrodenitrogenizing the diesel feedstock to reduce a sulfur content of the diesel feedstock and a nitrogen content of the diesel feedstock; passing the hydrodesulfurized and hydrodenitrogenized diesel feedstock to a hydrocracker comprising a metal-containing diesel hydrocracking catalyst comprising at least one zeolite to produce an isomerate fraction; and introducing the isomerate fraction to a separator to separate the isomerate fraction into a first stream enriched in n-paraffins and a second stream enriched in iso-paraffins and naphthenes.

Additional features and advantages of the embodiments described herein will be set forth in the detailed description which follows, and in part will be readily apparent to those skilled in the art from that description or recognized by practicing the embodiments described, including the detailed description and the claims which are provided infra.

BRIEF DESCRIPTION OF THE DRAWINGS

The following detailed description of specific embodiments of the present disclosure can be best understood when read in conjunction with the following drawings in which:

The FIGURE depicts a process and system comprising hydrocracking unit(s) and isomerate separator(s) in accordance with one or more embodiments of the present disclosure.

DETAILED DESCRIPTION

In embodiments, a process for reforming a diesel feedstock to convert diesel to a gasoline blending component includes hydrodesulfurizing and hydrodenitrogenating the diesel feedstock to reduce a sulfur content of the diesel feedstock and a nitrogen content of the diesel feedstock; hydrocracking the hydrodesulfurized and hydrodenitrogenated diesel feedstock over a metal-containing catalyst comprising at least one zeolite to produce an isomerate fraction; and separating the isomerate fraction into a first stream enriched in n-paraffins and a second stream enriched in iso-paraffins and naphthenes. Embodiments will now be described in further detail.

As used herein, the term "hydrocarbon oil" or "hydrocarbon feedstock" refers to an oily liquid composed mostly of a mixture of hydrocarbon compounds. Hydrocarbon oil may include refined oil obtained from crude oil, synthetic crude oil, bitumen, oil sand, shale oil, or coal oil. The term "refined oil" includes, but is not limited to, vacuum gas oil (VGO), deasphalted oil (DAO) obtained from a solvent deasphalting process, demetallized oil (DMO), light and/or heavy coker gas oil obtained from a coker process, cycle oil obtained from a fluid catalytic cracking (FCC) process, and gas oil obtained from a visbreaking process.

As used herein, the term "hydrocarbon" refers to a chemical compound composed entirely of carbon and hydrogen atoms. An expression such as "$C_x$-$C_y$ hydrocarbon" refers to a hydrocarbon having from x to y carbon atoms. For instance, a $C_1$-$C_5$ hydrocarbon includes methane, ethane, propane, iso-propane, butane, iso-butane, t-butane, and the pentanes.

As used herein, the term "diesel" refers to a middle distillate, largely produced from fractional distillation of crude oil between 180° C. and 370° C. Compositionally, diesel may include $C_9$-$C_{25}$ hydrocarbons, with a majority of the constituents being $C_{12}$-$C_{20}$, and an average at $C_{15}$-$C_{17}$. As used herein, the term "diesel feedstock" refers to a liquid composed mostly of diesel.

As used herein, the term "hydrogen/oil ratio" or "hydrogen-to-oil ratio" refers to a standard measure of the volume rate of hydrogen circulating through the reactor with respect to the volume of feed. The hydrogen/oil ratio may be determined by comparing the flow volume of the hydrogen gas stream and the flow volume of the hydrocarbon feed using standard flow meters.

As used herein, the term "liquid hourly space velocity" or "LHSV" refers to the ratio of the liquid flow rate of the hydrocarbon feed to the catalyst volume or mass.

As used herein, the term "research octane number" or "RON" refers to a property of fuels that is related to the amount of compression the fuel can withstand before detonating. RON may be calculated similar to the method found in Anderson et al., "Calculations of the Research Octane and Motor Gasolines from Gas Chromatographic Data and a New Approach to Motor Gasoline Quality Control," *Journal of the Institute of Petroleum*, vol. 52, pp. 83-93 (1972). In the method, each compound has an index, and the individual components are grouped. The octane number is calculated from the octane number of the group. The concentration of each group is multiplied with the octane number of each component and the sum gives the predicted octane number.

As used herein, the term "activity of the catalyst" or "catalytic activity" refers to the increase in the rate of the hydrocracking process due to the presence of the catalyst and may be approximated by the temperature at which 50% conversion of the feedstock is converted. A more highly active catalyst will have a lower such temperature.

Embodiments in accordance with the present disclosure generally relate to a process and system that includes converting and upgrading a middle distillate oil feedstock. As used herein, a middle distillate refers to a range of refined petroleum products obtained in the "middle" boiling range from about 180° C. to about 370° C. during the processing of crude oil. These processes may include hydrocracking the middle distillate oil feedstock over a metal catalyst to produce an isomerate fraction. In one or more embodiments, the distillate oil feedstock may be hydrodesulfurized and/or hydrodenitrogenated prior to being hydrocracked in order to reduce the sulfur and nitrogen content of the middle distillate oil feedstock. In one or more embodiments, the isomerate fraction may be further treated in a dehydrogenation reactor or a full catalytic reforming unit where the produced paraffins may undergo dehydrocyclization to cyclize the products of the produced isomerate fraction.

Thus, embodiments of the present disclosure are directed to converting diesel to gasoline. Because diesel is a desirable fuel, it is not conventionally hydrocracked or catalytically cracked. Rather, conventional hydrocracking processes were developed to convert heavy oil fractions as opposed to middle distillate fractions due to the high demand for middle distillates such as diesel oil. Therefore, considering that there will be a diesel surplus in the market and growing demand for chemicals, the present disclosure advantageously provides for the conversion of diesel to gasoline and/or high quality gasoline blending products, such as isomerate and aromatics rich gasoline, through hydrocracking.

As noted above, diesel is a middle distillate, largely produced from fractional distillation of crude oil between 180° C. and 370° C. Compositionally, diesel may include $C_9$-$C_{25}$ hydrocarbons, with a majority of the constituents being $C_{12}$-$C_{20}$, and an average at $C_{15}$-$C_{17}$. However, it is also envisioned that the hydrocracker feed of the present disclosure may more broadly encompass distillates that boil in the range of 100° C. to 420° C., such as having a lower limit of 100° C., 150° C., 180° C., or 200° C., and an upper limit of any of 350° C., 360° C., 375° C., 400° C., and 420° C. Such distillates are commonly referred to as light gas oils. While diesel is largely produced from distillation from 180° C. to 370° C., diesel is also produced from heavier fractions, including atmospheric gas oils, vacuum gas oils, and coker distillates, and it is envisioned that the feed to the hydrocracker may include downstream products from atmospheric gas oils, vacuum gas oils, and coker distillates. However, it is also appreciated that lighter fractions may also form part of the present feed. Thus, in one or more embodiments, the feed to a hydrocracker, as described herein, may be a feed that has been previously processed to arrive at the feed to the hydrocracker described herein. For example, for a majority of diesel that is produced from a middle distillate fractioned from 150° C. to 420° C., from 200° C. to 360° C., or from 250° C. to 350° C., such distillate may be hydrotreated prior to feeding the middle distillate to a hydrocracker.

In one or more embodiments, the middle distillates (distillates between 150° C. and 420° C. or between 200° C. and 360° C.) from the fractional distillation of crude oil are used as the feedstream for the hydrocracker. The middle distillates may be sent to a two-stage hydrotreating unit having hydrotreating in a first stage and hydrocracking in a second stage. The hydrotreating may be performed in the presence of a hydrotreating catalyst to significantly reduce the sulfur and nitrogen content of the feedstock, which may be referred to as desulfurization (or hydrodesulfurization) and denitrogenation (or hydrodenitrogenation). During hydrotreating processes, unsaturated hydrocarbons such as olefins, alkynes, and aromatics may also become saturated through reaction with hydrogen. Following hydrotreating and prior to hydrocracking, $H_2S$ and $NH_3$ produced in the hydrodesulfurization and hydrodenitrogenation may be separated from the hydrotreated effluent along with any light gases. The remaining effluent may be directed to the hydrocracker. In one or more embodiments, the effluent's sulfur content is less than or equal to 500 ppm by weight or less than or equal to 50 ppm by weight or less than or equal to 10 ppm by weight.

Further, in one or more embodiments, it is also envisioned that the feedstock may also include components that were processed from a heavier distillate that was subjected to one or more processing steps, such as vacuum gas oil being subjected to catalytic hydrocracking, to arrive at a feed for the present hydrocracking. Thus, it is envisioned that the feed to the present hydrocracking may include, in addition to middle distillates (as described above), downstream products from atmospheric gas oils, vacuum gas oils, and coker distillates. For example, it is envisioned that the feed may include the diesel pool formed in a conventional refinery.

The hydrocracking processes generally break the molecules of a feedstock (whether limited to middle distillates or including downstream products from heavier distillates) into smaller, i.e. lighter, molecules having higher average volatility and economic value than the feedstock. Thus, hydrocracking processes in accordance with the present disclosure generally comprise combining a distillate oil feed, such as described above, with hydrogen gas, and subjecting the mixture to elevated temperatures in the presence of a hydrocracking catalyst.

In one or more embodiments, the hydrocracking catalyst may include any a zeolite, a post modified zeolite, a metal containing zeolite, an unsupported metal catalyst, or a combination of two or more thereof. For example, the hydrocracking catalyst may include an ultra-stable Y-type (USY) zeolite, a post modified USY zeolite, a zeolite beta (BEA zeolite), an FAU zeolite, an MFI zeolite, or an MOR zeolite. Metals may include noble metals, i.e., Ru, Rh, Pd, Ag, Os, Ir, Pt, and Au. In embodiments, the metal containing zeolite comprises more than one such metal. In embodiments, the noble metal include Pt, Pd, or a mixture of Pt and Pd. An unsupported metal catalyst according to the present disclosure may include an active phase material including, in certain embodiments, Ni, W, Mo, Co, or a combination of two or more thereof.

In one or more embodiments, the hydrocracking may occur in a hydrocracking reactor that operates at a temperature from 250° C. to 450° C., from 300° C. to 400° C., from 280° C. to 400° C., or from 280° C. to 370° C. In one or more embodiments, the hydrocracking may occur in a hydrocracking reactor that operates at a hydrogen partial pressure of less than or equal to 90 bars, less than or equal to 80 bars, less than or equal to 70 bars, or less than or equal to 60 bars. In one or more embodiments, the hydrocracking may occur in a hydrocracking reactor that operates with a liquid hourly space velocity LHSV from $0.1\ h^{-1}$ to $10\ h^{-1}$, from $0.25\ h^{-1}$ to $5\ h^{-1}$, from $0.5\ h^{-1}$ to $5\ h^{-1}$, or from $0.5\ h^{-1}$ to $2\ h^{-1}$. In one or more embodiments, the hydrocracking may occur in a hydrocracking reactor that operates with a hydrogen/oil ratio from 500 standard liters per liter (StLt/Lt) to 2500 StLt/Lt, from 800 StLt/Lt to 2000 StLt/Lt, or from 1000 StLt/Lt to 1500 StLt/Lt.

In accordance with one or more embodiments, the hydrocracking process is accomplished over a metal catalyst, such as those described above to convert the middle distillate feedstock, such as a diesel oil feedstock, to an isomerate fraction stream as gasoline blending components. In one or more embodiments, the hydrocracked effluent may be an isomerate product stream comprising gasoline blend components, where the produced isomerate product stream has an octane number greater than or equal to 55, greater than or equal to 60, or greater than or equal to 70. This isomerate may be further processed to obtain value-added materials.

In accordance with one or more embodiments, the process for reforming a feedstock includes separating the isomerate fraction into a first stream enriched in n-paraffins and a second stream enriched in iso-paraffins and naphthenes. The first stream and the second stream may be separated from one another using an adsorption/desorption process, such as those disclosed in U.S. Pat. Nos. 4,176,053; 4,476,345; and 5,863,315; the entire content of each of which is incorporated herein by reference. In a typical process, the isomerate fraction is allowed to flow over an adsorbent capable of retaining n-paraffins while allowing iso-paraffins to pass through. For instance, a zeolitic molecular sieve may be used as the adsorbent. The n-parafffins may then be desorbed from the adsorbent using a non-sorbable purge gas under controlled pressure and/or temperature conditions. For instance, desorption pressure may be from 0.3 MPa to 3 MPa, and desorption temperature may be from 170° C. to 400° C.

Referring now to the FIGURE, a process flow diagram according to one or more embodiments of the present disclosure is shown. While the present disclosure focuses on the upgrading of diesel by hydrocracking and separation of the resulting isomerate stream (as described above), the present FIGURE is provided to show the modifications that can be made to an existing refinery to convert hydrotreating units to perform the presently described hydrocracking to convert diesel surplus into gasoline.

As shown in the FIGURE, crude oil 10 is introduced to distillation column 100. Crude oil 10 may be any source of crude oil and distillation column 100 can be any type of separation unit capable of separating a hydrocarbon stream (specifically crude oil 10) into component parts, based on targeted cut points of distillation. An example of distillation column 100 includes an atmospheric distillation column. Distillation column 100 can be operated to separate acid gas, naphtha, kerosene/jet, (light) gas oil, and atmospheric residue 38 that may be directed to vacuum distillation column 150. Vacuum distillation column 150 can be employed to separate vacuum gas oils such as light vacuum gas oil, heavy vacuum gas oil, and vacuum residue, under vacuum conditions.

As shown in the FIGURE, distillation column 100 can produce, for example, acid gas 15, light fraction (naphtha) stream 20, jet/kerosene 25, light gas oil 30, heavy gas oil 35, and atmospheric residue 38. Vacuum distillation column 150 can produce, for example, light vacuum gas oil 40, heavy vacuum gas oil 50, and vacuum residue stream 60 from the atmospheric residue 38. In one or more embodiments, light fraction stream 20 can have a T95% cut point of less than or equal to 240° C. As used herein, the term "195% cut point" refers to the temperature at which at least 95% of the fraction has evaporated. Light fraction stream 20 may contain naphtha. Acid gas stream 15 may be distilled and directed to a gas treating unit 125. Acid gas generated during crude oil and natural gas processing typically includes hydrogen sulfide and other undesirable compounds. The removal of acid gas via acid gas stream 15 reduces components such as hydrogen sulfide, carbon dioxide ($CO_2$), carbonyl sulfide (COS), carbon disulfide ($CS_2$) and mercaptans (RSH) from gas and liquid hydrocarbon streams.

Light fraction stream 20 may be directed to a naphtha hydrotreating unit 175 to produce a heavy naphtha stream 23 and a light naphtha stream 24. Light naphtha stream 24 is directed to catalytic reformer and/or isomerization unit 950 to produce reformed product stream 26 that is then introduced to gasoline pool 1000. Heavy naphtha stream 23 may be directed to a catalytic reforming unit.

Jet/kerosene stream 25 may have a cut point in the range of 180° C. to 260° C., for example, and light gas oil 30 can have a T95% cut point in the range between 340° C. and 380° C. The jet/kerosene stream 25 and light gas oil stream 30 are each directed to diesel hydrocracking unit 900. While jet/kerosene stream 25 and light gas oil stream 30 would conventionally be directed to a jet/diesel hydrotreater for hydrodesulfurization and hydrodenitrogenation to reduce the sulfur and/or nitrogen content prior to feeding the effluent into a diesel pool, in accordance with embodiments of the present disclosure, jet/kerosene stream 25 and light gas oil stream 30 may instead be directed to diesel hydrocracking unit 900. Diesel hydrocracking unit 900 comprises a hydrotreating reactor, separation unit, and hydrocracking reactor. The separation unit may include, for example, a flash drum, gas-liquid separators and/or stripping columns and/or fractionation to remove dissolved gases such as hydrogen sulfide and ammonia from the hydrotreated effluent.

In the first stage of the diesel hydrocracking unit 900, the jet/kerosene stream 25 and light gas oil 30 are subjected to hydrodesulfurization and hydrodenitrogenation in the hydrotreating reactor to reduce and/or remove sulfur and nitrogen. In one or more embodiments of the present disclosure, a hydrotreating reactor may operate at temperatures in the broad range from 250° C. to 450° C. or from 300° C. to 450° C. Reaction zone pressures may be in the range from 25 bar to 150 bar, and the hydrogen partial pressure may be from 35 bar to 100 bar. Contact times usually correspond to liquid hourly space velocities (LHSV) in the range from 0.2 $hr^{-1}$ to 6.0 $hr^{-1}$ or from 0.2 $hr^{-1}$ to 4.0 $hr^{-1}$. The space velocity may be dependent upon the feedstock composition.

In one or more embodiments of the present disclosure, the hydrotreating catalyst may be any suitable catalyst. Hydrotreating catalysts of some embodiments may comprise one or more metals selected from the group consisting of molybdenum, tungsten, cobalt, and nickel. The active metals may be supported to provide a greater surface area. More than one type of hydrotreating catalyst may be used in the same reactor. In some embodiments, that are not shown, multiple hydrotreating reactors may be used in series within a unit 900. In embodiments where multiple hydrotreating reactors are used, each reactor may be primarily directed to the removal of a different component, such as hydrodesulfurization and hydrodenitrogenation.

In certain embodiments in which an objective is hydrodenitrogenation, alumina or silica-alumina based catalysts loaded with Ni—Mo or Ni—W active metals, or combinations thereof, are used. In embodiments in which the objective is to remove nitrogen and to increase the conversion of hydrocarbons, silica, alumina, titania, zeolite, or a combination of two or more thereof are used as catalysts, with active metals including Ni—Mo, Ni—W, or combinations thereof.

In diesel hydrocracking unit 900, the hydrotreated effluent stream comprising hydrotreated products from jet/kerosene stream 25 and light gas oil stream 30 may be directed to a separating unit where additional $H_2S$, $NH_3$, any light gases including $C_1$-$C_4$ hydrocarbons, and any naphtha may be removed. The separated effluent, including fractions with an initial nominal boiling point temperature of about 180° C. and final boiling point temperatures ranging from about 340° C. to about 420° C., is sent to the hydrocracking reactor to undergo cracking reactions. The hydrocracking reactor may include a zeolite, a post modified zeolite catalyst, a metal containing zeolite, an unsupported metal catalyst, or a combination of two or more thereof.

The hydrocracking in the diesel hydrocracking unit 900 may be performed at a reaction temperature from 250° C. to 450° C., from 300° C. to 400° C., or from 280° C. to 370° C. In one or more embodiments, the hydrocracking may occur in a hydrocracking reactor that operates at a hydrogen partial pressure of less than or equal to 100 bars, less than or equal to 90 bars, less than or equal to 80 bars, less than or equal to 70 bars, or less than or equal to 60 bars. In one or more embodiments, the hydrocracking may occur in a hydrocracking reactor that operates with a liquid hourly space velocity LHSV from $0.1\ h^{-1}$ to $10\ h^{-1}$, from $0.25\ h^{-1}$ to $5\ h^{-1}$, from $0.5\ h^{-1}$ to $5\ h^{-1}$, or from $0.5\ h^{-1}$ to $2\ h^{-1}$. In one or more embodiments, the hydrocracking may occur in a hydrocracking reactor that operates with a hydrogen/oil ratio from 500 standard liters per liter (StLt/Lt) to 2500 StLt/Lt, from 800 StLt/Lt to 2000 StLt/Lt, or from 1000 StLt/Lt to 1500 StLt/Lt.

After the second stage (hydrocracking) of diesel hydrocracking unit 900, effluent 34 may include an isomerate fraction, including n-paraffins, iso-paraffins, naphthenes, and aromatics. Effluent 34 may be fed to separation zone 1100, which separates the isomerate fraction of the effluent 34 into an n-paraffin-rich stream 92 and an iso-paraffin-rich stream 94. The n-paraffin-rich stream 92 may be fed to steam cracking unit 1150 to produce light olefin stream 96. The iso-paraffin-rich stream 94 may be directed to reforming/isomerization unit 950 prior to being directed to gasoline pool 1000, sent directly to gasoline pool 1000, or sent to fluid catalytic cracking (FCC) unit 1200 to produce light olefin stream 96.

Light vacuum gas oil 40 may have a T95% cut point in the range from 400° C. to 430° C. Light vacuum gas oil 40 can be introduced to cracking unit 200, which may be selected from, for example, a catalytic hydrocracking unit, a fluid catalytic cracking unit, and the like. Hydrocracking unit 200 may also receive heavy gas oil 35. The effluent may be fractionated by fractionator unit of hydrocracking unit 200 into light fraction 75 and gas oil 80. Upgraded light fraction 75 may contain the naphtha range hydrocarbons and kerosene range hydrocarbons present in light vacuum gas oil 40. Upgraded light fraction 75 may be mixed with treated light fraction stream 24 and introduced to reforming/isomerization unit 950 prior to being directed to gasoline pool 1000.

In at least one embodiment, upgraded light fraction 75 may be introduced to gasoline 1000 without first mixing with treated light fraction stream 24.

Heavy vacuum gas oil 50 may have a T95% cut point of greater than or equal to 565° C. Vacuum residue stream 60 may have a T5% cut point of greater than or equal to 565° C. Vacuum residue stream 60 contains the heaviest fraction of crude oil. Heavy vacuum gas oil 50 may be introduced to vacuum gas oil hydrotreater 225 which may comprise a hydrotreating reactor and separator. The produced effluent from the hydrotreating reactor of hydrotreating unit 225 may be separated to remove gas oils which may be directed to the diesel hydrocracking reactor 900 via stream 53. Treated heavy vacuum gas oil stream 54 may be fed to catalytic cracking unit 250, which may be, for example, a fluid catalytic cracking unit, etc. The effluent of catalytic cracker 250, which may include cycle oils, for example, may be separated into catalytically cracked gasoline stream 58 and light cracked distillate stream 56. Catalytically cracked gasoline stream 58 may then be fed to hydrocracked gasoline pool 1050 and light and heavy cracked distillate stream 56 may be fed to hydrocracker 200 with light vacuum gas oil stream 40. In one or more embodiments, light cracked distillate stream 56 may be fed directly to diesel hydrocracking unit 900 via stream 57.

Vacuum residue stream 60 may be introduced to resid (residual) upgrading unit 400. Resid upgrading unit 400 may be any process unit capable of upgrading a heavy fraction stream. Examples of resid upgrading unit 400 include resid fluid catalytic cracking (FCC) unit, residue hydrocracker, resid hydrodesulfurization (RHDS) hydrotreater, visbreaker, coker, gasifier, and solvent extractor. Resid upgrading unit 400 may produce resid upgraded product 90 and gas oil stream 65 which may be directed to diesel hydrocracking unit 900. Gas oil stream 65 may be directed to diesel hydrocracking unit 900 to be subjected to the hydrotreating, separation, and hydrocracking steps described above. Vacuum gas oil stream 66 may be directed to diesel hydrocracking unit 900 to be subjected to the hydrotreating, separation, and hydrocracking steps described above.

According to an aspect, either alone or in combination with any other aspect, a process for reforming a diesel feedstock to convert diesel to a gasoline blending component includes hydrodesulfurizing and hydrodenitrogenizing the diesel feedstock to reduce a sulfur content of the diesel feedstock and a nitrogen content of the diesel feedstock; hydrocracking the hydrodesulfurized and hydrodenitrogenized diesel feedstock over a metal-containing diesel hydrocracking catalyst comprising at least one zeolite to produce an isomerate fraction; and separating the isomerate fraction into a first stream enriched in n-paraffins and a second stream enriched in iso-paraffins and naphthenes.

According to a second aspect, either alone or in combination with any other aspect, a process for reforming a diesel feedstock to convert diesel to a gasoline blending component includes introducing the diesel feedstock to a treater for hydrodesulfurizing and hydrodenitrogenizing the diesel feedstock to reduce a sulfur content of the diesel feedstock and a nitrogen content of the diesel feedstock; passing the hydrodesulfurized and hydrodenitrogenized diesel feedstock to a hydrocracker comprising a metal-containing diesel hydrocracking catalyst comprising at least one zeolite to produce an isomerate fraction; and introducing the isomerate fraction to a separator to separate the isomerate fraction into a first stream enriched in n-paraffins and a second stream enriched in iso-paraffins and naphthenes.

According to a third aspect, either alone or in combination with any other aspect, the process further comprises steam cracking at least a portion of the first stream to convert at least a portion of the n-paraffins to light olefins.

According to a fourth aspect, either alone or in combination with any other aspect, the process further comprises adding at least a portion of the second stream to a gasoline pool.

According to a fifth aspect, either alone or in combination with the third aspect, the process further comprises adding at least a portion of the second stream to a feedstock for a fluid catalytic cracking process or a catalytic reforming process.

According to a sixth aspect, either alone or in combination with any other aspect, the fluid catalytic cracking process converts at least a portion of the feedstock for the fluid catalytic cracking process to propylene.

According to a seventh aspect, either alone or in combination with the fifth aspect, the sulfur content of the diesel feedstock is reduced to less than or equal to 500 ppm by weight in the hydrodesulfurizing step.

According to an eighth aspect, either alone or in combination with any other aspect, the sulfur and nitrogen contents of the diesel feedstock are reduced to less than or equal to 10 ppm by weight in the hydrodesulfurizing step.

According to a ninth aspect, either alone or in combination with the seventh aspect, the diesel feedstock boils at a temperature from 150° C. to 420° C.

According to a tenth aspect, either alone or in combination with any other aspect, the diesel feedstock boils at a temperature from 180° C. to 375° C.

According to an eleventh aspect, either alone or in combination with any other aspect, the metal-containing diesel hydrocracking catalyst comprises a noble metal.

According to a twelfth aspect, either alone or in combination with any other aspect, the noble metal is selected from the group consisting of platinum, palladium, ruthenium, gold, and a combination of two or more thereof.

According to a thirteenth aspect, either alone or in combination with any other aspect, the hydrocracking occurs in a hydrocracking reactor that operates at a temperature from 280° C. to 400° C.

According to a fourteenth aspect, either alone or in combination with any other aspect, the hydrocracking occurs in a hydrocracking reactor that operates at pressure less than or equal to 60 bars.

According to a fifteenth aspect, either alone or in combination with any other aspect, the hydrocracking reactor is operated at a liquid hourly space velocity from 0.5 per hour to 5 per hour.

According to a sixteenth aspect, either alone or in combination with any other aspect, the at least one zeolite comprises at least one of an ultra-stable Y-type (USY) zeolite, a post modified USY zeolite, a zeolite beta (BEA zeolite), an FAU zeolite, an MFI zeolite, or an MOR zeolite.

According to a seventeenth aspect, either alone or in combination with any other aspect, the at least one zeolite comprises at least one post-modified zeolite.

According to an eighteenth aspect, either alone or in combination with any other aspect, the sulfur content of the diesel feedstock is reduced to less than or equal to 500 ppm by weight in the treater.

According to a nineteenth aspect, either alone or in combination with any other aspect, the sulfur and nitrogen contents of the diesel feedstock are reduced to less than or equal to 10 ppm by weight in the treater.

EXAMPLES

Using embodiments described above, an exemplary hydrocracking pilot plant test was conducted, as follows. The following examples are merely illustrative and should not be interpreted as limiting the scope of the present disclosure.

Comparative Example 1

A hydrocracking pilot plant test was conducted using a deeply hydrodesulfurized diesel oil as a feedstock. The properties of the feedstock is shown in Table 1.

TABLE 1

| Comparative Example 1 Feedstock Properties | |
|---|---|
| Property | Value |
| Density @ 15.6° C. (g/cm$^3$) | 0.83 |
| Sulfur content (ppm by weight) | < 10 |
| Nitrogen content (ASTM D-4629) (ppm by weight) | 21 |
| Simulated Distillation (D2887) | Temperature (° C.) |
| 0 wt. % | 110 |
| 5 wt. % | 177 |
| 10 wt. % | 203 |
| 30 wt. % | 255 |
| 50 wt. % | 287 |
| 70 wt. % | 318 |
| 90 wt. % | 362 |
| 95 wt. % | 379 |
| 100 wt.% | 414 |
| 2D GC × GC Composition | wt. % |
| Paraffins | 52.68 |
| Naphthenes | 25.26 |
| Mono-aromatics | 19.45 |
| Di-aromatics | 2.11 |
| Tri-Plus aromatics | 0.5 |

The experiments were conducted at 60 bars of hydrogen partial pressure, a temperature of 355° C., a LHSV of 1 h$^{-1}$, and a hydrogen to gas oil ratio of 1,000 StLt/Lt. The catalyst was a zeolite containing catalyst with platinum as an active phase metal.

The diesel oil feedstock of Comparative Example 1 and product distillation data are shown in Table 2. The diesel is fully converted to an isomerate fraction comprising gasoline range products, as evidenced by the final boiling point of the product of 186° C., which is the expected boiling point for gasoline.

TABLE 2

| Comparative Example 1 Product Data | | |
|---|---|---|
| Concentration Off | Feedstock Temperature (° C.) | Product Temperature (° C.) |
| 0 wt.% | 110 | 34 |
| 5 wt.% | 177 | 59 |
| 10 wt.% | 203 | 69 |
| 30 wt.% | 255 | 89 |
| 50 wt.% | 287 | 103 |
| 70 wt.% | 318 | 119 |
| 90 wt.% | 362 | 141 |

TABLE 2-continued

Comparative Example 1 Product Data

| Concentration Off | Feedstock Temperature (° C.) | Product Temperature (° C.) |
| --- | --- | --- |
| 95 wt.% | 379 | 149 |
| 100 wt.% | 414 | 186 |

Two-dimensional gas chromatography (2D GC×GC) was used to identify the n-paraffins, iso-paraffins, olefins, naphthenes, and aromatics. Under this analysis, the n-paraffins and iso-paraffins combined accounted for 76.9 wt. % of the products, naphthenes accounted for 22 wt. %, and aromatics accounted for 1 wt. %. The products were also analyzed for compositional type using PIONA analysis, in accordance with ASTM D6730, and a research octane number (RON) of 64.5 was calculated from this data. As shown in Table 3, under the PIONA analysis, n-paraffins accounted for 14.3 wt. % of the products, iso-paraffins accounted for 52.1 wt. %, naphthenes accounted for 28.8 wt. %, and aromatics accounted for 3.5 wt. %. Thus, the process of Comparative Example 1 may sufficiently serve to simultaneously hydrocrack the diesel oil feedstock, hydrogenate the aromatics to naphthenes, crack naphthenes, and subsequently isomerize naphthenes to result in a final isomerate fraction with greater than or equal to 50 wt. % iso-paraffins.

TABLE 3

PIONA of the Isomerate of Comparative Example 1

| Column No. | n-Paraffins (wt. %) | iso-paraffins (wt. %) | Naphthenes (wt. %) | Aromatics (wt. %) |
| --- | --- | --- | --- | --- |
| 3 | 0.006 | 0 | 0 | 0 |
| 4 | 0.044 | 0.061 | 0 | 0 |
| 5 | 0.352 | 0.539 | 0.385 | 0 |
| 6 | 4.144 | 6.281 | 4.303 | 0.708 |
| 7 | 4.983 | 18.714 | 16.066 | 1.3 |
| 8 | 3.832 | 17.046 | 5.346 | 0.966 |
| 9 | 0.991 | 9.069 | 3.007 | 0.464 |
| 10 | 0.183 | 1.058 | 0.087 | 0.063 |
| Total | 14.53 | 52.77 | 29.19 | 3.51 |

Inventive Example 1

The isomerate fraction produced in Comparative Example 1 was subjected to an n-paraffin separation step in accordance with the process and reactor system described above. Two fractions were obtained: 1. n-paraffin rich stream, 2. iso-paraffin rich stream. Table 4 summarizes the PIONA data for the iso-paraffin rich stream from which the n-paraffin stream was separated. The RON increased by about 14 points, relative to Comparative Example 1, to 81, with the separation of n-paraffins. Further, the n-paraffin rich stream may be an advantageous feedstream for steam cracking to produce light olefins. The iso-paraffin rich stream may be reformed in a catalytic reforming unit to produce an aromatic rich gasoline fraction, sent directly to the gasoline pool, or sent to an FCC unit to produce light olefins. Therefore, the resulting product streams provide desirable value-added substances.

TABLE 4

PIONA of the Iso-Paraffin Rich Stream of Example 1.

| Column No. | n-Paraffins (wt. %) | iso-paraffins (wt. %) | Naphthenes (wt. %) | Aromatics (wt. %) |
| --- | --- | --- | --- | --- |
| 3 | 0 | 0 | 0 | 0 |
| 4 | 0.003 | 0.071 | 0 | 0.809 |
| 5 | 0.020 | 0.626 | 0.447 | 1.492 |
| 6 | 0.241 | 7.292 | 4.995 | 1.105 |
| 7 | 0.289 | 21.725 | 18.65 | 0.531 |
| 8 | 0.222 | 19.789 | 6.207 | 0.072 |
| 9 | 0.058 | 10.528 | 3.49 | 0 |
| 10 | 0.011 | 1.228 | 0.101 | 0 |
| 11 | 0 | 0 | 0 | 0 |
| 12 | 0 | 0 | 0 | 0 |
| Total | 0.84 | | 33.89 | 4.01 |

It is noted that recitations in the present disclosure of a component of the present disclosure being "operable" or "sufficient" in a particular way, to embody a particular property, or to function in a particular manner, are structural recitations, as opposed to recitations of intended use. More specifically, the references in the present disclosure to the manner in which a component is "operable" or "sufficient" denotes an existing physical condition of the component and, as such, is to be taken as a definite recitation of the structural characteristics of the component.

Having described the subject matter of the present disclosure in detail and by reference to specific embodiments, it is noted that the various details disclosed in the present disclosure should not be taken to imply that these details relate to elements that are essential components of the various embodiments described in the present disclosure. Further, it will be apparent that modifications and variations are possible without departing from the scope of the present disclosure, including, but not limited to, embodiments defined in the appended claims.

The singular forms "a", "an" and "the" include plural referents, unless the context clearly dictates otherwise.

Throughout this disclosure ranges are provided. It is envisioned that each discrete value encompassed by the ranges are also included. Additionally, the ranges which may be formed by each discrete value encompassed by the explicitly disclosed ranges are equally envisioned.

As used in this disclosure and in the appended claims, the words "comprise," "has," and "include" and all grammatical variations thereof are each intended to have an open, non-limiting meaning that does not exclude additional elements or steps.

As used in this disclosure, terms such as "first" and "second" are arbitrarily assigned and are merely intended to differentiate between two or more instances or components. It is to be understood that the words "first" and "second" serve no other purpose and are not part of the name or description of the component, nor do they necessarily define a relative location, position, or order of the component. Furthermore, it is to be understood that the mere use of the term "first" and "second" does not require that there be any "third" component, although that possibility is contemplated under the scope of the present disclosure.

What is claimed is:

1. A process for reforming a diesel feedstock to convert diesel to a gasoline blending component, comprising:
   hydrodesulfurizing and hydrodenitrogenizing the diesel feedstock to reduce a sulfur content of the diesel feedstock and a nitrogen content of the diesel feedstock;

hydrocracking the hydrodesulfurized and hydrodenitrogenized diesel feedstock over a metal-containing diesel hydrocracking catalyst comprising at least one zeolite to produce an isomerate fraction;

separating the isomerate fraction into a first stream enriched in n-paraffins and a second stream enriched in iso-paraffins and naphthenes; and adding at least a portion of the second stream to a feedstock for a fluid catalytic cracking process.

2. The process of claim 1, further comprising steam cracking at least a portion of the first stream to convert at least a portion of the n-paraffins to light olefins.

3. The process of claim 1, further comprising adding at least a portion of the second stream to a gasoline pool.

4. The process of claim 1, wherein the fluid catalytic cracking process converts at least a portion of the feedstock for the fluid catalytic cracking process to propylene.

5. The process of claim 1, wherein the sulfur content of the diesel feedstock is reduced to less than or equal to 500 ppm by weight in the hydrodesulfurizing step.

6. The process of claim 1, wherein the diesel feedstock boils at a temperature from 150° C. to 420° C.

7. The process of claim 1, wherein the metal-containing diesel hydrocracking catalyst comprises a noble metal selected from the group consisting of platinum, palladium, ruthenium, gold, and a combination of two or more thereof.

8. The process of claim 1, wherein the hydrocracking occurs in a hydrocracking reactor that operates at a temperature from 280° C. to 400° C., at pressure less than or equal to 60 bars, and at a liquid hourly space velocity from 0.5 per hour to 5 per hour.

9. The process of claim 1, wherein the at least one zeolite comprises at least one of an ultra-stable Y-type (USY) zeolite, a post modified USY zeolite, a zeolite beta (BEA zeolite), an FAU zeolite, an MFI zeolite, or an MOR zeolite.

10. A process for reforming a diesel feedstock to convert diesel to a gasoline blending component, comprising:

introducing the diesel feedstock to a treater for hydrodesulfurizing and hydrodenitrogenizing the diesel feedstock to reduce a sulfur content of the diesel feedstock and a nitrogen content of the diesel feedstock;

passing the hydrodesulfurized and hydrodenitrogenized diesel feedstock to a hydrocracker comprising a metal-containing diesel hydrocracking catalyst comprising at least one zeolite to produce an isomerate fraction;

introducing the isomerate fraction to a separator to separate the isomerate fraction into a first stream enriched in n-paraffins and a second stream enriched in iso-paraffins and naphthenes; and adding at least a portion of the second stream to a feedstock for a fluid catalytic cracking process.

11. The process of claim 10, further comprising steam cracking at least a portion of the first stream to convert at least a portion of the n-paraffins to light olefins.

12. The process of claim 10, further comprising adding at least a portion of the second stream to a gasoline pool.

13. The process of claim 10, wherein the fluid catalytic cracking process converts at least a portion of the feedstock for the fluid catalytic cracking process to propylene.

14. The process of claim 10, wherein the sulfur and nitrogen contents of the diesel feedstock are reduced to less than or equal to 10 ppm by weight in the treater.

15. The process of claim 10, wherein the diesel feedstock boils at a temperature from 150° C. to 420° C.

16. The process of claim 10, wherein the metal-containing diesel hydrocracking catalyst comprises a noble metal selected from the group consisting of platinum, palladium, ruthenium, gold, and a combination of two or more thereof.

17. The process of claim 10, wherein the hydrocracking occurs in a hydrocracking reactor that operates at a temperature from 280° C. to 400° C., at pressure less than or equal to 60 bars, and at a liquid hourly space velocity from 0.5 per hour to 5 per hour.

18. The process of claim 10, wherein the at least one zeolite comprises at least one of an ultra-stable Y-type (USY) zeolite, a post modified USY zeolite, a zeolite beta (BEA zeolite), an FAU zeolite, an MFI zeolite, or an MOR zeolite.

* * * * *